United States Patent
Takahashi et al.

(10) Patent No.: US 6,555,836 B1
(45) Date of Patent: Apr. 29, 2003

(54) METHOD AND APPARATUS FOR INSPECTING BUMPS AND DETERMINING HEIGHT FROM A REGULAR REFLECTION REGION

(75) Inventors: Fumiyuki Takahashi, Kawasaki (JP); Hiroyuki Tsukahara, Kawasaki (JP); Yoshitaka Oshima, Kawasaki (JP); Youji Nishiyama, Kawasaki (JP); Takashi Fuse, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 09/533,235

(22) Filed: Mar. 22, 2000

(30) Foreign Application Priority Data

Apr. 6, 1999 (JP) ............................................ 11-099440

(51) Int. Cl.⁷ ............................................. G01N 21/86
(52) U.S. Cl. ............................. 250/559.19; 250/559.22; 250/559.27; 356/602; 356/608; 356/612
(58) Field of Search ..................... 250/559.05, 559.07, 250/559.09, 559.19, 559.22, 559.23, 559.45, 559.46, 559.27; 356/376, 602, 608, 612; 348/87, 126; 382/154; 702/159, 166, 170, 172

(56) References Cited

U.S. PATENT DOCUMENTS

| | | | | |
|---|---|---|---|---|
| 4,428,676 A | * | 1/1984 | Chastang et al. | 356/354 |
| 5,392,110 A | * | 2/1995 | Yojima et al. | 356/1 |
| 5,774,224 A | * | 6/1998 | Kerstens | 356/394 |
| 5,859,924 A | * | 1/1999 | Liu et al. | 382/145 |
| 6,028,673 A | * | 2/2000 | Nagasaki et al. | 356/376 |
| 6,069,701 A | * | 5/2000 | Hashimoto | 356/376 |
| 6,177,998 B1 | * | 1/2001 | Svetkoff et al. | 356/376 |

FOREIGN PATENT DOCUMENTS

JP        6-137825        5/1994

* cited by examiner

Primary Examiner—Stephone B. Allen
Assistant Examiner—Christopher W. Glass
(74) Attorney, Agent, or Firm—Armstrong, Westerman & Hattori, LLP.

(57) ABSTRACT

A method of inspecting bumps provided on a surface of an object to be inspected includes the steps of: (a) irradiating a first irradiation beam on said object in an oblique direction and (b) imaging a first reflected beam from said object so as to obtain a first reflection image including a first reflection region and a height data of said bump corresponding to said first regular reflection region produced by a part of the first reflected beam reflected near an apex of the bump. The method further includes the steps of (c) shifting a position of said first regular reflection region in said first reflection image in accordance with a value derived from said height data and said predetermined angle, (d) extracting said first regular reflection region within a predetermined region from said first reflection image after said step c), and (e) detecting a height of said bump based on said height data corresponding to the extracted first regular reflection region. Also disclosed is an apparatus for performing the disclosed method.

12 Claims, 11 Drawing Sheets

| CONDITION | VALUE OF HEIGHT DATA |
|---|---|
| $h1<\beta$ AND $h2<\beta$ | $H+(h1+h2)/2$ |
| $h1<\beta$ AND $h2>\beta$ | $H+h1$ |
| $h1>\beta$ AND $h2<\beta$ | $H+h2$ |
| $h1>\beta$ AND $h2>\beta$ | INDETERMINATE |

METHOD AND APPARATUS FOR INSPECTING BUMPS AND DETERMINING HEIGHT FROM A REGULAR REFLECTION REGION

BACKGROUND OF THE INVENTION

1. Field of the Invention

The present invention generally relates to a method and an apparatus for inspecting bumps provided on an object to be inspected. The present invention particularly relates to detecting height of bumps provided on a surface of a semiconductor chip or a wafer of a flip-chip bonding type or on a package, such as a BGA, provided with bumps serving as mounting terminals.

Recently, in order to realize high-density mounting of input/output terminals of LSI chips, there is a greater interest in technologies such as flip-chip bonding and a package provided with bumps serving as connection terminals.

However, such technologies have a certain drawback. That is, any variation of the size of the bumps produced during manufacturing of the bumps may result in a problematic aspect during mounting of the semiconductor chip or the package. That is to say, the neighboring bumps may be short-circuited or the chip and the package may be badly connected to the substrate.

In order to prevent such a problem, it is necessary to find any defects of the bumps before mounting the semiconductor chip or the package. However, the semiconductor chip may be provided with bumps amounting to several thousands or more, in which case visual inspection of the bumps is almost impossible. Thus, there is a need for an apparatus which can automatically inspect any defect of the bumps.

2. Description of the Related Art

FIG. 1 is a schematic diagram showing a bump inspection device of the related art. The bump inspection device includes a movable inspection stage 26, a laser beam generator 10, a scanner 11, a first objective lens 12, a second objective lens 13 and a PSD (Position Sensitive Detector) 14. An object to be inspected is represented by a wafer 1, which is placed on the movable inspection stage 26, however, the object to be inspected can be any type of semiconductor device provided with bumps. In FIG. 1, for the sake of clarity, only one bump 2 is shown on the wafer 1.

The laser beam generator 10 generates a laser beam which serves as an irradiation beam 3. The scanner 11 scans the irradiation beam 3 in a fixed direction. The irradiation beam 3 is irradiated onto the bump 2 via the first objective leans 12. The second objective lens 13 receives the beam reflected at the bump 2. The PSD 14 receives the reflected beam 4 from the second objective lens and outputs information related to an imaging position and brightness of the reflected beam 4 in the form of electric signals.

Now an operation of the bump inspection device will be described with reference to FIG. 1. The scanner 11 scans the irradiation beam 3 from the laser beam generator 10 in a direction perpendicular to the plane of drawing (main scanning direction). Then, the scanned beam is, via the first objective lens 12, irradiated on a surface of the wafer 1 provided with the bump 2. The beam reflected from the surface of the wafer 1 is imaged on the PSD 14 via the second objective lens 13. The PSD 14 outputs electrical signals corresponding to the position and the brightness of a spot imaged thereon.

Also, for every scanning operation of the scanner 11, the stage 26 is moved in a direction parallel to the plane of drawing (sub-scan direction). Thus, the irradiation beam 3 is scanned for an entire area to be inspected on the wafer 1. Since the position of the spot of the reflected beam 4 imaged on the PSD 14 varies with the height of the bump 2, the height of the bump 2 can be detected from the scanning position of the irradiation beam 3 and the output signals from the PSD 14. Such technology, in which the size of the bump is measured by triangulation, is known from Japanese laid-open patent application No. 6-137825.

Referring to FIGS. 2A and 2B, the image from the PSD 14 and the height profile will be described for the case where the entire inspection area is scanned.

FIG. 2A shows an image (reflection image) produced by sequentially storing the signals from the PSD 14 into a memory (not shown), which signals indicating the brightness of the reflected beam 4. Here, for the sake of clarity, it is assumed that there is only one bump 2 as shown in FIG. 1 and no other bumps exist around the bump 2. Also, the shadow 6 of the bump will in fact be narrow in the middle, but since the shape of the shadow does not affect essential aspects of the present invention, the shadow 6 is shown as an ellipse.

FIG. 2A also shows a regular reflection region 5 which appears as a bright region. The regular reflection region 5 is a region in which a regularly reflected portion of the reflected beam 4 is imaged at the PSD 14. The regularly reflected portion of the reflected beam 4 corresponds to a portion of the irradiation beam 3 regularly reflected near the apex of the bump 2. The bump shadow 6 is a region where the reflected beam 4 does not reach the PSD. The region around the bump shadow 6 becomes a bright region due to a portion of the reflected beam 4 reflected at the surface of the wafer 1.

It is to be noted that this reflection image is produced by the reflected beam 4 which originates from the irradiation beam 3 irradiated in an oblique direction with respect to the surface of the wafer 2 on which the bump 2 is provided. Therefore, in the reflected image, the reflected beam 4 regularly reflected near the apex of the bump 2 will appear in the bump shadow 6 at a position shifted towards the direction of travel of the irradiation beam 3. The regular reflection region 5 represents such shifted position.

FIG. 2B is a diagram showing a height profile along line a–a' for the reflected image shown in FIG. 2A. In the figure, the abscissa indicates the position and the ordinate indicates the height-profile. As has been described above, the height for each scanning point can be derived from the scanning position of the irradiation beam 3 and the position of the beam spot on the PSD 14. The height profile is obtained by sequentially storing thus derived height data for each scanning position into the memory.

In FIG. 2B, it can be seen that the height profile shows a curve having a relatively high value at a position corresponding to the regular reflection region 5. On the contrary, the curve has a relatively low value at parts corresponding to other region of the bump shadow 6. However, in practice, the height profile does not exist for the region corresponding to the bump shadow 6 since no data can be obtained from such a region. That is to say, the region in the bump shadow 6 wherefrom the height data can be obtained is only the regular reflection region 5 where the reflected light 4 is imaged on the PSD 14.

Referring now to FIGS. 3A to 6, drawbacks of the related art will be described.

In case where only one bump is provided and no other bumps are provided around that bump, the reflection image will include one reflection region. Such a region is shown as the regular reflection region 5 in FIG. 2A. Therefore, there is no problematic aspect when deriving the height of the bump 2. However, a wafer or a package normally has a number of bumps provided at a predetermined pitch. Thus, the irradiation beam 3 will be reflected on the plurality of bumps in a multiple manner. Therefore, a number of reflection regions other than the regular reflection region will appear in the reflection image due to multiple reflection.

The multiple reflection occurs in a various patterns in dependence of the size and pitch of the bumps and the direction of the irradiation beam. The following description relates to a few typical patterns of the multiple reflection.

FIGS. 3A and 3B are diagrams showing an example of multiple reflection. FIG. 3A shows the wafer 1 and bumps 2a to 2c. When the irradiation beam 3a is incident near the apex of the bump 2b, the beam will be reflected in a path shown as a reflected beam 4a. However, when the irradiation beam is scanned in a direction shown by an irradiation beam 3b, the beam will be reflected in a path shown by a reflected beam 4b. The reflected beam 4b is reflected at the bump 2b towards the bump 2b, reflected at the bump 2a towards the wafer 1, reflected at the surface of the wafer 1 towards the bump 2b, and again reflected off at the bump 2b. Then, the reflected beam 4b is imaged on the PSD 14 via the second objective lens 13 shown in FIG. 1.

FIG. 3B is a diagram showing another example of multiple reflection. When the irradiation beam is scanned in a direction shown by an irradiation beam 3c, the beam will be reflected in a path shown as a reflected beam 4c. The reflected beam 4c is reflected at the bump 2b towards the bump 2c and then reflected off at the bump 2c. Then, the reflected beam 4c is imaged on the PSD via the second objective lens 13.

FIGS. 4A and 4B are diagrams showing a reflection image and a height-profile, respectively, for a case of multiple reflection.

FIG. 4A is a diagram showing a reflection image including multiple reflection regions 51b, 52b, 51c. Regular reflection regions 5a to 5c are regions in which regularly reflected portions of the reflected beams 4a are imaged at the PSD 14. The regularly reflected portion of the reflected beam 4a corresponds to a portion of the irradiation beam 3a regularly reflected near the apex of the bump 2. The multiple reflection regions 51b, 52b, 51c are reflection regions produced by multiple reflection indicated in FIGS. 3A and 3B. Also, in FIG. 4A, bump shadows 6a to 6c are shown as a single shadow region.

FIG. 4B is a diagram showing a height profile along line a–a' for the reflected image shown in FIG. 4A. In the figure, the abscissa indicates the position and the ordinate indicates the height-profile. Since the multiple reflection regions 51b, 52b, 51c are reflection regions in which portions of the reflected light are imaged on the PSD 14, height data for the multiple reflection regions 51b, 52b, 51c can be detected. However, as shown in FIG. 4B, the height data for the multiple reflection region is irrelevant to the height of the bumps 2a to 2c. Therefore, if the height of the bump is derived based on the multiple reflection region, the obtained result will be erroneous.

In order to solve this problem, the multiple reflection regions 51b, 52b, 51c may be masked in order to extract the regular reflection regions 5a to 5c.

FIG. 5 is a diagram showing a reflection image provided with windows 7a and 7b. The windows 7a and 7b are provided for masking regions other than predetermined areas.

A detecting area may be limited by providing the window 7a in the multiple reflection region. However, since the window 7a includes the multiple reflection region 51b, an effect of the multiple reflection cannot be entirely removed. Therefore, there is a need to reduce the size of the window to the window 7b. That is to say, in the case shown in the figure, since the multiple reflection region 51b exists in close proximity to the regular reflection region 5b, it is not preferable to set a window having greater size.

It is to be noted that the position of the regular reflection region 5b will alter depending on the height of the bump 2b, as shown in FIGS. 6A and 6B. FIGS. 6A and 6B are diagrams showing a shift of the position of the regular reflection region in case where the bump has a reduced height. If the bump 2b has a smaller height compared to other bumps 2a and 2c, as shown in FIG. 6A, the regular reflection region 5b resulting from the reflected beam 4 will be shifted towards right in the reflection image, as shown in FIG. 6B.

Thus, although the position of the regular reflection region 5b is altered depending on the height of the bump 2b, the window 7b cannot have a size exceeding a predetermined size for avoiding the multiple reflection regions. Therefore, in order to measure the height of the bump accurately, it is not sufficient to simply limit the detection area by providing a window at a predetermined position of the reflection image.

SUMMARY OF THE INVENTION

Accordingly, it is a general object of the present invention to provide a method and device for inspecting bumps which can accurately measure the height of the bumps by setting a window which can exclude an effect of multiple reflection for a variation of the height of the bumps.

It is another and more specific object of the present invention to provide a method of inspecting the height of the bump which is not affected by multiple reflection between a number of bumps.

In order to achieve the above objects according to the present invention, a method of inspecting bumps provided on a surface of an object to be inspected includes the steps of:

a) irradiating a first irradiation beam on said object in an oblique direction at a predetermined angle with respect to said surface;

b) imaging a first reflected beam from said object so as to obtain a first reflection image including a first regular reflection region and a height data of said bump corresponding to said first regular reflection region, said first regular reflection region being produced by a part of the first reflected beam reflected near an apex of the bump;

c) shifting a position of said first regular reflection region in said first reflection image in accordance with a value derived from said height data and said predetermined angle;

d) extracting said first regular reflection region within a predetermined region from said first reflection image after said step c); and e) detecting a height of said bump based on said height data corresponding to the extracted first regular reflection region.

With the method described above, the position of the first reflection region is shifted in the first reflection image based on the corresponding height data and the predetermined angle of irradiation. Thus, the position of the first regular reflection region is determined independent of the height of the bump. Then, a window is set at the determined position so as to mask the multiple reflection region upon extracting the first regular reflection region.

In other words, the position of the first regular reflection is shifted by a value derived from the value of the corresponding height data and the predetermined angle. Therefore, since any height error data resulting from multiple reflection can be removed, the height of the bump can be detected with a higher accuracy.

The present invention also provides an apparatus for inspecting the bump using such a method.

Other objects and further features of the present invention will be apparent from the following detailed description when read in conjunction with the accompanying drawings.

DETAILED DESCRIPTION OF THE PREFERRED EMBODIMENTS

In the following, principles and embodiments of the present invention will be described with reference to the accompanying drawings.

The following description relates to an embodiment of a method of inspecting bumps formed on a wafer. However, the present invention is not limited to an application to bumps on the wafer, but can also be applied to bumps on a chip after dicing or to bumps used as mounting terminals provided on a package.

A first embodiment of a method of inspecting bumps will be described with reference to FIGS. 7 to 9.

Figure 7:
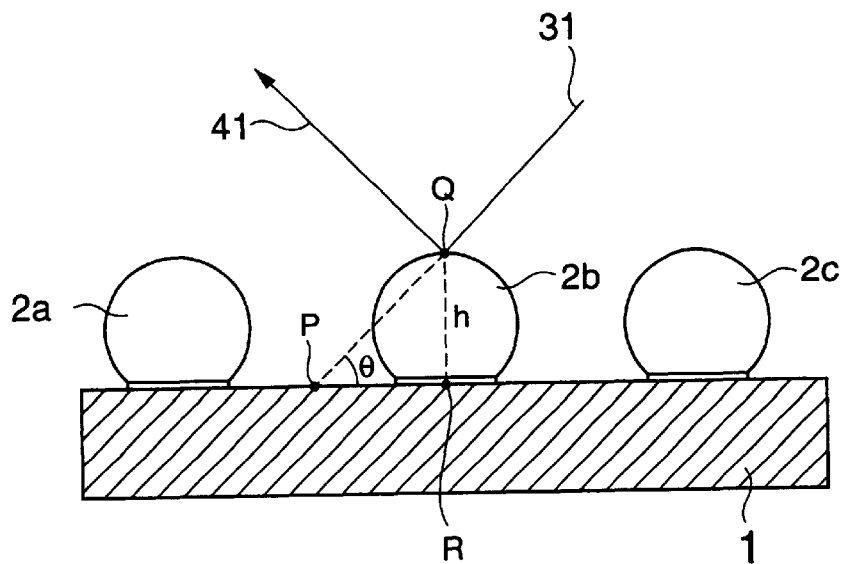
FIG. 7 is a diagram used for explaining an amount of shift of a first regular reflection region.

FIG. 7 is a diagram used for explaining an amount of shift of a first regular reflection region. FIG. 7 shows an object to be inspected, which includes a wafer 1 and bumps 2a to 2c provided on the wafer 1. Also, number of bumps may vary depending on the type of the object to be inspected, but, for the sake of clarity, only with three bumps are illustrated in the present embodiment.

A first irradiation beam 31 is obtained by scanning a laser beam. The first irradiation beam 31. scans the object to be inspected in a direction perpendicular to the plane of drawing (main scanning direction). Also, for every scanning operation, a stage is moved in a direction parallel to the plane of drawing (sub-scan direction). Thus, the wafer 1 is irradiated over the entire area to be inspected.

It is to be noted that the entire area of the wafer 1 may also be scanned without moving the stage and simply by two-dimensional scanning of the irradiation beam 31. Also, instead of the scanned laser beam, the first irradiation beam 31 may be a sheet-like beam having a linear shape resulting from a use of a cylindrical lens. In this case, in order to irradiate the entire area of the object to be inspected, either the sheet-like beam is scanned or the stage is moved. Then, in order to detect the imaging position of a first reflected beam 41, it is necessary to use an element, such as a CCD, capable of detecting a two-dimensional position.

The first irradiation beam 31 is irradiated obliquely in a direction forming an angle of 45 degrees with the surface of the wafer 1 on which the bumps 2a to 2c are provided. The angle need not be 45 degrees as long as it forms an oblique angle, but it is known that more multiple reflection tends to occur as the angle approaches zero. The angle near right angle is also not desirable since the resolution of the bump height detection will be reduced.

Thus, the first irradiation beam 31 is irradiated on the entire inspection area of the wafer 1. Then, the brightness data of the imaged portion of the first reflected beam 41, reflected at the wafer 1, are sequentially stored into the memory so as to form the first reflection image. Also, the height data corresponding to the heights of the bumps 2a to 2c, respectively, are detected by applying the triangulation principle to the imaging position of the first reflected beam 41 and the first irradiation beam 31. Then, the height data are sequentially stored in the memory at locations corresponding to the first reflection image so as to form a height data memory region. That is to say, the memory stores the height data, each of which corresponding to each pixel block of the first reflection image. At memory locations different from those of the first reflection image, the height data memory region is formed so as to correspond to the first reflection image.

Figure 8A:
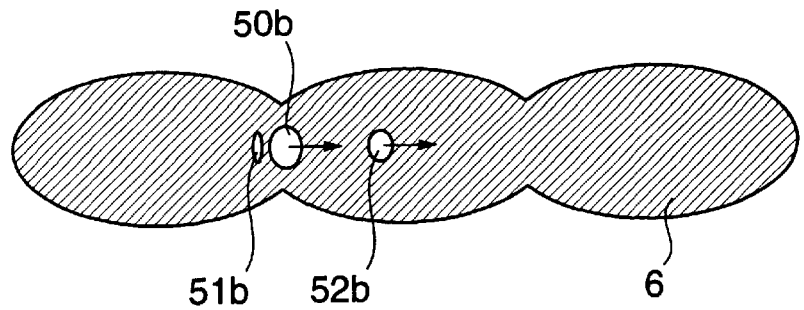
FIGS. 8A to 8C are diagrams used for explaining how the first regular reflection region is shifted.

Referring now to FIG. 8A, a first reflection image of the first reflected beam 41 is described for a case where the entire inspection area of the wafer 1 is scanned.

Figure 1:
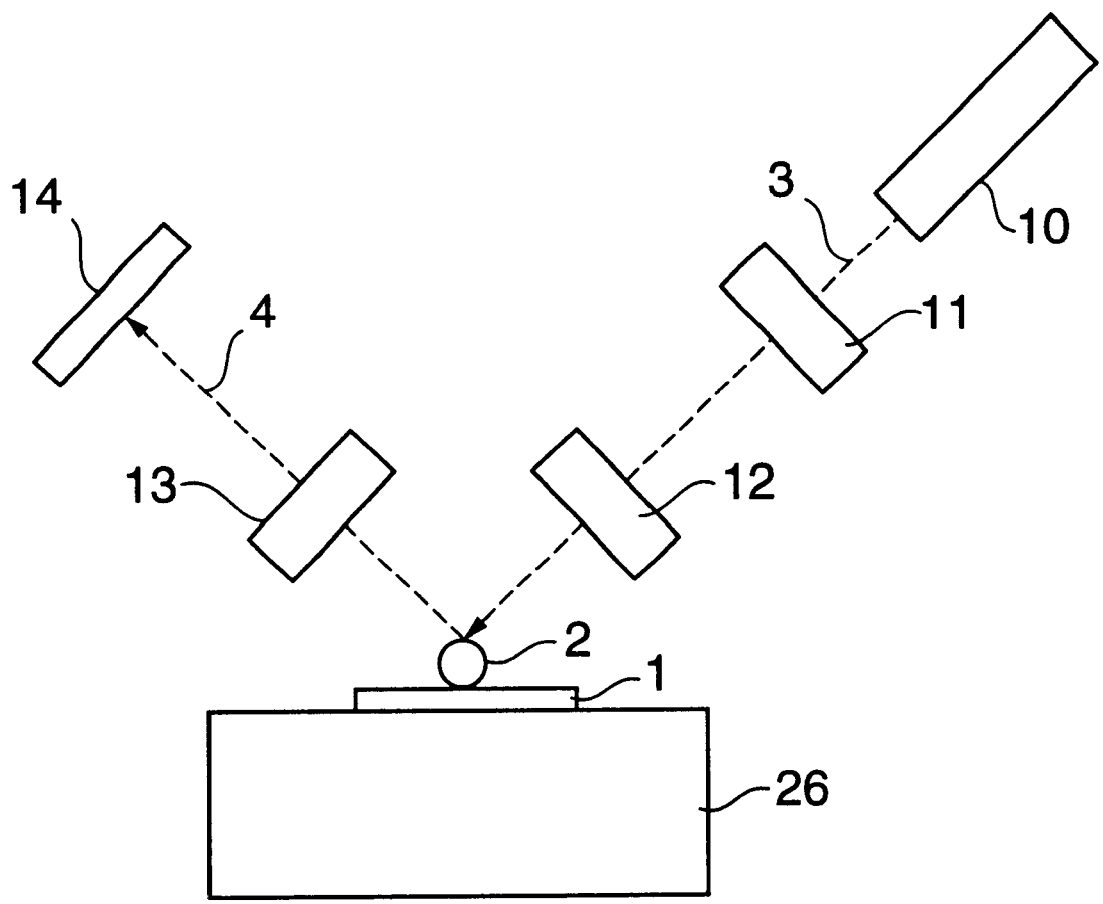
FIG. 1 is a schematic diagram showing a bump inspection device of the related art.
Figure 2A:
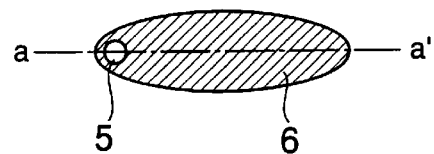
FIGS. 2A and 2B are diagrams showing a reflection image and a height-profile, respectively, for a case where there is only a one bump.
Figure 2B:
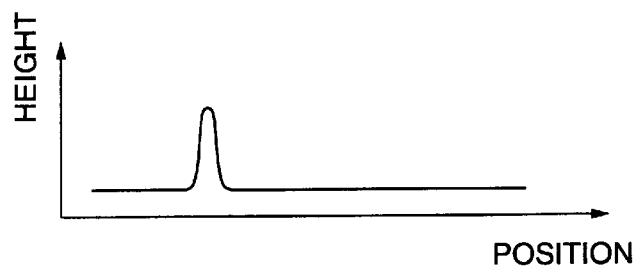
Figure 3A:
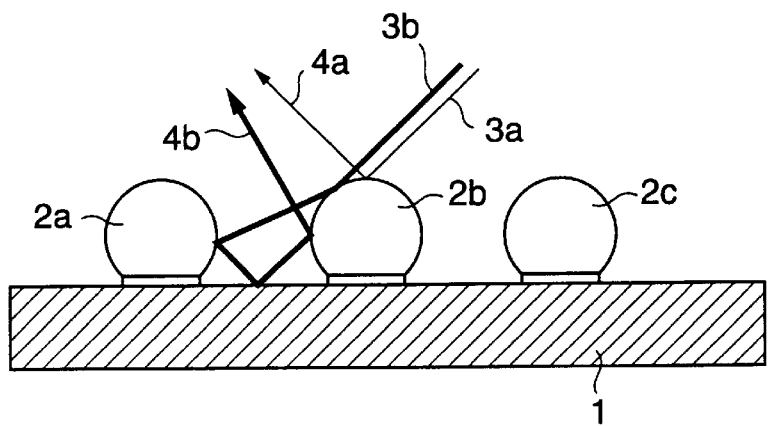
FIGS. 3A and 3B are diagrams showing examples of multiple reflection.
Figure 3B:
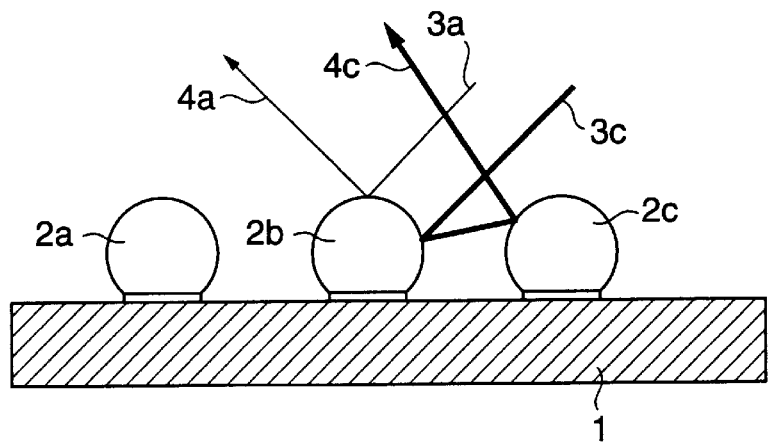
Figure 4A:
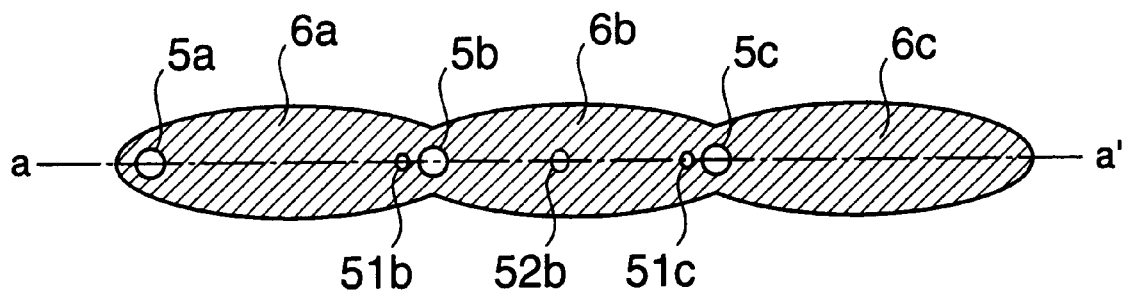
FIGS. 4A and 4B are diagrams showing a reflection image and a height-profile, respectively, for a case of multiple reflection.
Figure 4B:
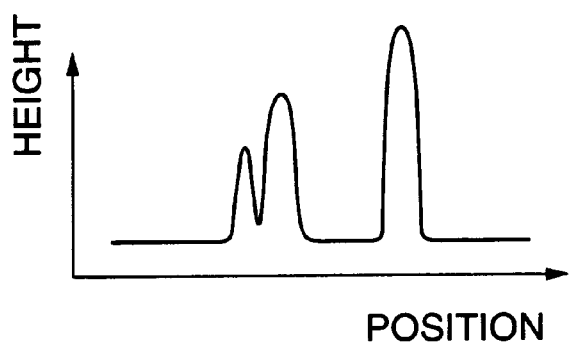
Figure 5:
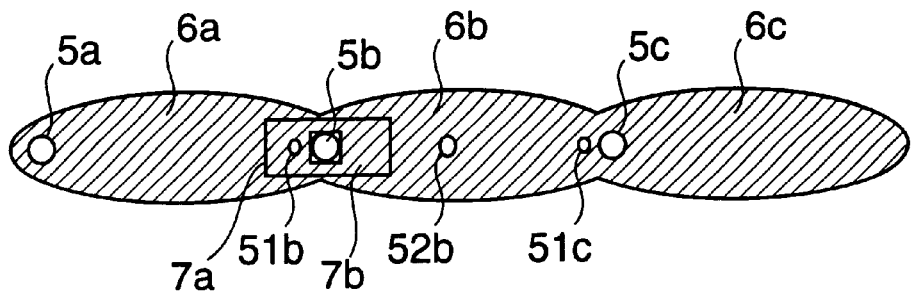
FIG. 5 is a diagram showing a reflection image in which a window is provided.
Figure 6A:
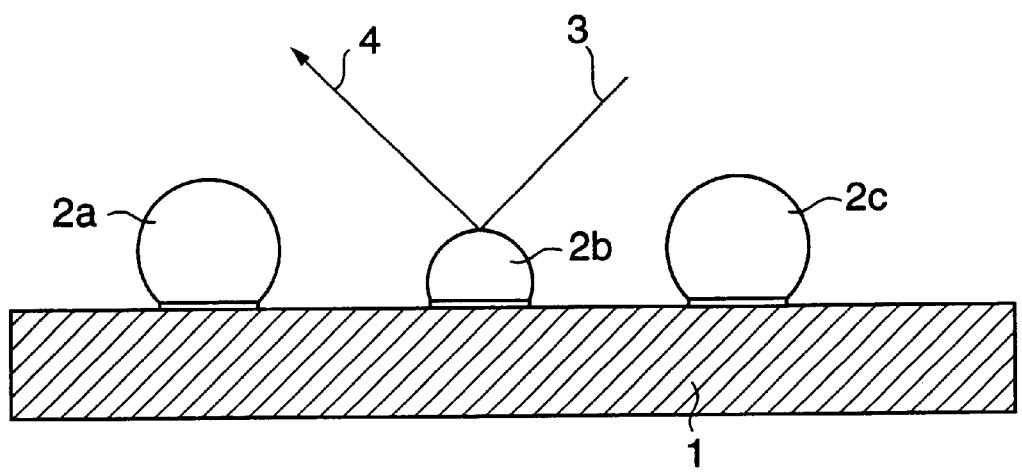
FIGS. 6A and 6B are diagrams showing a shift of the position of the regular reflection region in case where one of the bumps has a reduced height.
Figure 6B:
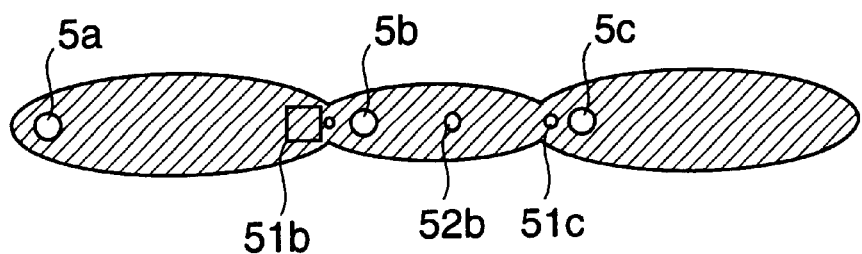

FIG. 8A is a diagram showing a shift of a first regular reflection region. In the figure, elements similar to those shown in FIG. 4A are indicated by like reference numerals. It is to be noted that a first regular reflection region 50b shown in FIG. 8A corresponds to the regular reflection region 5b shown in FIG. 4A. In FIG. 8A, for the sake of clarity, only the first regular reflection region 50b and the multiple reflection regions 51b, 52b are shown, which are reflection regions of a reflection first reflected at the bump 31.

In the first reflection image shown in FIG. 8A, the position of the first regular reflection region 50b is shifted towards the direction of travel of the first irradiation beam 31 with respect to the bump shadow 6. Here, the first regular reflection region 50b is produced by the first reflected beam 41 reflected at a position near the apex of the bump 2b. Referring again to FIG. 7, for the first reflection image, an amount of shift of the first regular reflection region 50b from the central position of the bump 2b will be described.

In FIG. 7, a point Q is a point at which the first reflection light 41 is reflected and a distance h represents a height data of the point Q, which is a distance between the reference surface (the surface of the wafer 1) and the point Q. Also, a point P represents a point of intersection of an extension of the first irradiation beam 31 and the surface of the wafer 1. A point R represents a point at which a perpendicular line from the point Q intersects the surface of the wafer 1. An angle $\theta$ represents an angle formed between the first irradiation beam 31 and the surface of the wafer 1. Then, the length of a line PR can be expressed as:

$$PR = h/\tan(\theta).$$

Also, since the position of the point P serves as a positional reference point in the first reflection image, the first reflected beam 41 reflected at the point Q appears in the first reflection image as a reflected beam at point P. In this case, an amount of shift of the first regular reflection region 50b in the first reflection image corresponds to a distance between the point R and the point P.

Therefore, if the position of the first regular reflection region 50b is compensated with an amount corresponding to the line PR, the first regular reflection region 50b matches a position corresponding to the central position of the bump 2b. In detail, the first regular reflection region 50b may be shifted by an amount corresponding to $h/\tan(\theta)$ in a direction opposite to the first irradiation beam 31.

With such a compensation of the position of the first regular reflection region 50b to the central position of the bump, the position of the first regular reflection region 50b can be fixed independent of the height of the bump 2b. In other words, the position of point P is shifted in dependence of the height of the bump 2b, but the central position of the bump 2b is fixed independent of its height. Therefore, the first regular reflection region 50b can be fixed in the first reflection image by shifting the first regular reflection region 50b to the position corresponding to the central position of the bump 2b in the first reflection image.

Figure 8B:
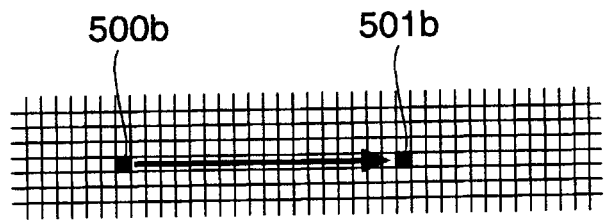

Referring now to FIG. 8B, the method of moving the first regular reflection region 50b will be described in detail.

FIG. 8B is a diagram showing how the first regular reflection region is shifted in the first reflection image. A pixel block 500b represents a block of pixels in the first reflection image, which constitutes the first regular reflection region 50b or the multiple reflection regions 51b, 52b before the shifting operation. Also, a pixel block 501b represents a pixel block in the first reflection image, which constitutes the first regular reflection region 50b or the multiple reflection regions 51b, 52b after the shifting operation. The number of pixels included in a pixel block can be altered depending on number of pixels in the first reflection image or on a required accuracy or speed.

The shifting operation of the first regular reflection region 50b in the first reflection image includes an alteration of the first reflection image itself. It is to be understood that the shifting operation also includes an alteration of the image by transferring the first reflection image to another memory location and then shifting the first regular reflection region 50b into that memory location.

Now, a method of moving the first regular reflection region and the multiple reflection regions will be described.

For the first regular reflection region 50b or the multiple reflection regions 51b, 52b, which are reflection regions from the bumps 2a to 2c, a height data stored in the height data memory region is read out for each pixel block 500b. For the first regular reflection region 50b, the height data corresponding to the pixel block 500b substantially corresponds to the height of the apex of the bump 2b. However, for the multiple reflection regions 51b, 52b, the height data corresponding to the pixel block 500b is determined based on the height of the last reflection point from the surface of the wafer 1 and on the scanning position of the first irradiation beam 31. Also, if the position of the region to be shifted within the first reflection image is roughly specified in advance by, for example, CAD data, the position of the region to be shifted within the first reflection image can be rapidly processed.

Then, the pixel block 500b is moved from its original position to a shifted position shown as the pixel block 501b. The shifting operation is implemented in the first reflection image in a direction opposite to the first irradiation beam 31 by an amount corresponding to $h/\tan(\theta)$, which can be derived based on its position, the read-out height data h and the angle $\theta$.

In detail, the brightness data corresponding to the pixel block before the shifting operation is replaced by the brightness data corresponding to the pixel block after the shifting operation. Also, along with the shifting of the pixel block 500b in the first reflection image, the height data corresponding to the pixel block 500b is moved within the height data memory region. Thereby, the relationship between the pixel block 500b before the shifting operation and the corresponding height data remains substantially the same for the relationship between the pixel block 501b after the shifting operation and the corresponding height data. All of the above-described steps are repeated for the first regular reflection region 50b and the multiple reflection regions 51b, 52b.

If the relationship of the height data that the pixel block corresponds to 500b remains the same for the pixel block 501b after the shifting operation, the height data need not be moved within the height data memory region. Also, instead of shifting the first regular reflection region and/or the multiple reflection regions in the first reflection image, the position of the height data corresponding to the first regular reflection region and/or the multiple reflection regions, respectively, may be moved in the height data memory region. In such a case, the height data in the height data memory region corresponding to the pixel block 500b before the shifting operation will be moved to a position in the height data memory region corresponding to the pixel block 501b after the shifting operation.

Also, as a result of repeating the above-described steps, a plurality of pixel blocks may accidentally shifted to the same pixel block due an effect such as noise. In this case, since there will be a plurality of height data having different values in the same pixel block after the shifting operation, the accuracy will be lowered. Therefore, it is desirable to predetermine the height data for such a pixel block. The method of determining the height data for a pixel block will be described with reference to FIG. 9.

Figures 9, 10:
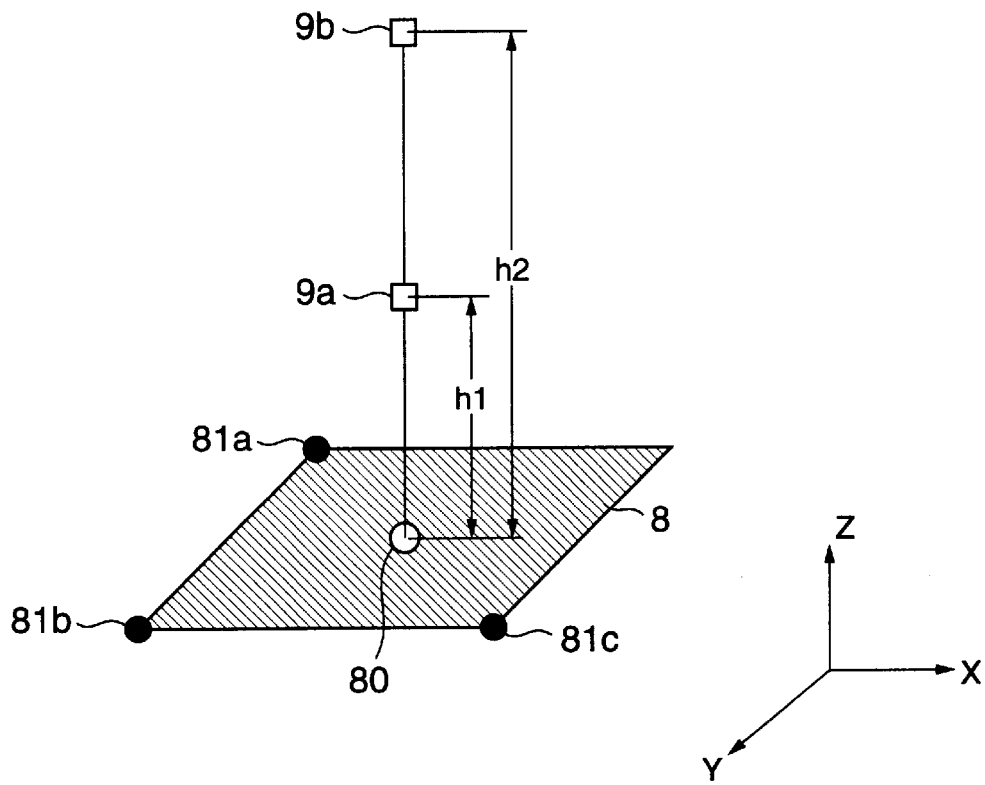
FIG. 9 is a diagram showing how the height data is determined when there is an overlap of a plurality of pixel blocks.
FIG. 10 shows a chart indicating conditions of β and value of height data.

FIG. 9 is a diagram showing how the height data is determined when there is an overlap of a plurality of pixel blocks. Here, it is assumed that there is an overlap of two pixel blocks. Points 81a to 81c each represents a point indicating the height and the position of the pixel block. The points 81a to 81c indicate the position and height data of the pixel blocks neighboring the pixel block at which an overlap has occurred as a result of the shifting operations of the pixel blocks.

The position in the XY-direction of each of the points 81a to 81c corresponds to the position in the first reflection image and the position in the Z-direction corresponds to the height data at that pixel block. The neighboring pixel blocks are those pixel blocks in the first regular reflection region 50b or the multiple reflection regions 51b, 52b which are at small distances from a point indicating a position of a pixel block 80. At least three neighboring pixel blocks are chosen from those pixel blocks having height data which may be uniquely determined before and after the shifting operation.

FIG. 9 also shows a virtual plane 8 passing through the points 81a to 81c. The point 80 indicates a position corresponding to the pixel block at which an overlap has occurred due to the shifting operation. The position of the point 80 in the XY-direction corresponds to a position of the overlapped pixel block in the first reflection image and the position in the Z-direction corresponds to a projection of the overlapped pixel block the virtual plane 8. The height data of the pixel block position is represented by H.

A point 9a represents a value of the height data of one of the pixel blocks causing the overlap. A point 9b represents a value of the height data of the other one of the pixel blocks causing the overlap. The points 9a and 9b both lie on a line passing through the position 80 and extending in the Z-direction. An arrow h1 represents a distance between the point 9a and the pixel block position 80. An arrow h2 represents the distance between the point 9b and the pixel block position 80.

With the above-described definitions, if there is no effect such as noise, the points 9a, 9b should exist at a small distance from the virtual plane 8 defined by the height data of the neighboring pixel blocks. Thus, as shown in FIG. 10, the value of the height data of the overlapped pixel block is determined in accordance with a predetermined value β.

It is to be noted that the value of β is set to a minimum resolution of the height data. This will be explained with reference to a chart shown in FIG. 10. When the height data is expressed with 256 tones, the height data of the points 81a to 81c will be 105, 97 and 100, respectively. It is assumed that the height H at the point 80 is 102.5, and the height data at the points 9a, 9b are 103 and 110, respectively. Then, the values of h1 and h2 will be 0.5 and 7.5, respectively. If β is set to a value of 1, the condition satisfies h1<β and h2>β. Therefore, the height data at the overlapped pixel block will be H+hi, which can be numerically expressed as 102.5+0.5, thus giving a value of 103.

The above explanation relates to a case where two pixel blocks overlap on a single pixel block. However, the same process can be applied for a case where three pixel blocks overlap on a single pixel block.

Figure 8C:
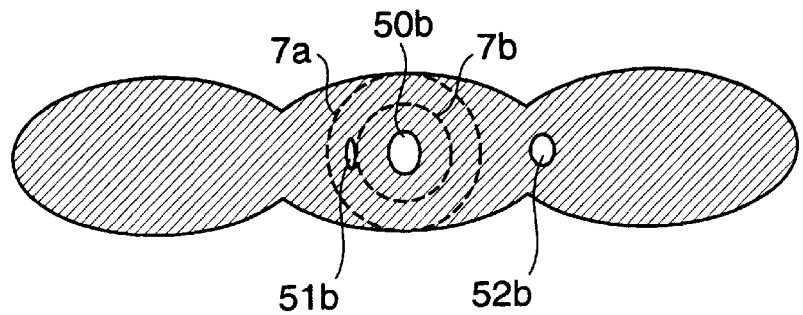

FIG. 8C is a diagram showing the first reflection image after the shifting operation. FIG. 8C particularly shows how a window is set after the shifting operation of the first regular reflection region. The first regular reflection region 50b is compensated to a position corresponding to the central position of the bump 2b in the first reflection image.

In FIG. 8A, the multiple reflection region 51b is located at a position relatively close to the first regular reflection region 50b. In FIG. 8B, the multiple reflection region 51b and the first regular reflection region 50b are shifted with a greater distance between them than in the case shown in FIG. 8A. This is because, as shown in FIG. 8B, the amount of shift of the multiple reflection region 51b is smaller than that of the first regular reflection region 50b, since the height data of the multiple reflection region 51b is smaller than that of the first regular reflection region 50b. This facilitates the setting of the window as described below.

Now, the setting of the window will be described with reference to FIG. 8C. FIG. 8C shows windows 7a, 7b for extracting only a part of the image within a predetermined region and for masking a region outside the predetermined region.

In order to set the window, it is necessary to determine its central position, shape and size. First, the central position may be determined from the bump shadow 6. For example, the position of the center of gravity is derived from the shape of the bump shadow 6 and this center of gravity is determined as a central point of the bump. Then, the window is set to a predetermined size centering on the thus-determined central point.

Secondly, a CAD data may be used. The first reflection image is positioned with a CAD data, which has been prepared in advance. Then, the central position of the window is set according to the position information of the bump in the CAD data.

The preferred shape of the window depends on the shape of the bump to be inspected. This is because, in order to remove the multiple reflection region, it is preferable that the shape of the window corresponds to the first regular reflection region. Also, the shape of the first regular reflection region depends of the shape of the bump to be inspected. For instance, if the bump has a spherical shape, it is preferable that the window is circular. If the bump has a cylindrical shape or a rectangular parallelepiped shape, the shape of the window should correspond to the shape of the first regular reflection region. Also, for the same reason, it is preferable that the size of the window corresponds to the size of the first regular reflection region.

In FIG. 8C, the window 7a covers the first regular reflection region 50b and also the multiple reflection region 51b. This implies that an accurate height of the bump 2b cannot be detected uniquely. In order to avoid this, the window 7b may be used, which only covers the first regular reflection region 50b. As has been described above, since the distance between the multiple reflection region 51b and the first regular reflection region 50b is made greater as a result of the compensation, the setting of the window 7b is facilitated.

As has been described above, the first reflection image is masked according to the bump shadow 6 of the first reflection image or to the CAD data, so as to extract only the first regular reflection region 50b from the first reflection image including the multiple reflection regions 51b, 52b. A reference is made to a CAD data, in order to determine which first regular reflection region corresponds to which actual bump of the object to be inspected.

Finally, the height data corresponding to the pixel block in the extracted first regular reflection region is read out from the height data memory region. Then, the data having an extremely high value due to noise is removed. Thereafter, the height data having the highest value is detected as a height of the bump 2b.

Also, if the height data in the height data memory region is moved without shifting the first regular reflection region and the multiple reflection region in the first reflection image, the height data memory region is masked by the mask shown in FIG. 8C. Then, the height data in the window 7b is extracted and the similar process is carried out to determine the height of the bump 2b.

Now, a second embodiment of the method of inspecting the bump will be described with reference to FIGS. 11A to 13B. The second embodiment can-be applied to a case where a bump has been deformed. First, some drawbacks will be described for the case where there is a bump deformation.

Figure 11A:
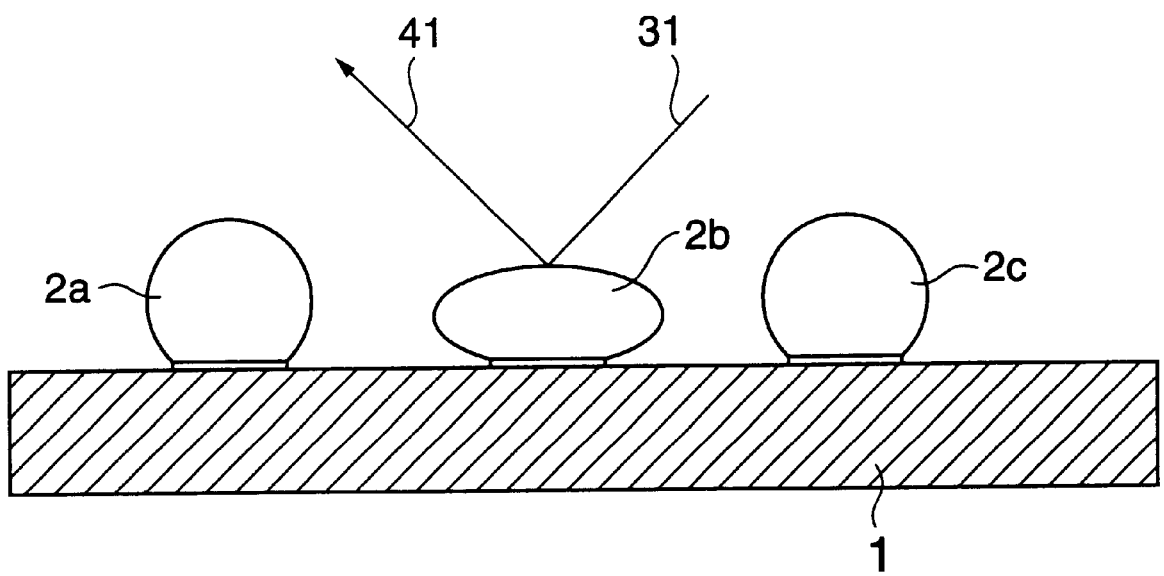
FIGS. 11A and 11B are diagrams showing an enlarged regular reflection region in case of a deformation of a bump.
Figure 11B:
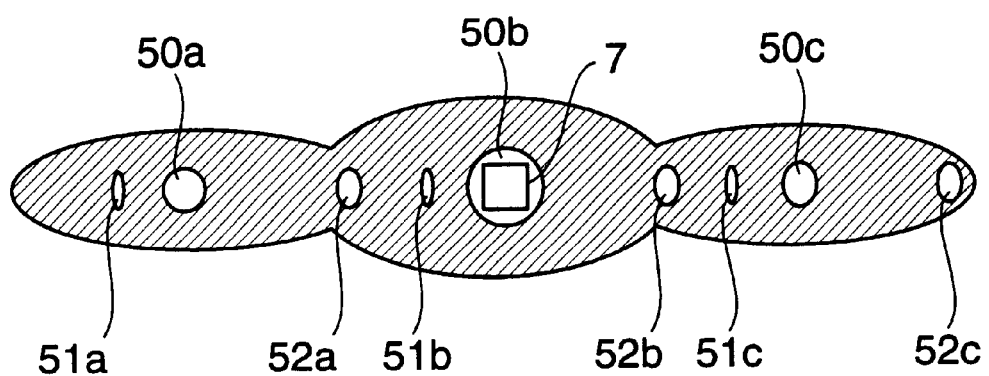

FIGS. 11A and 11B are enlarged diagrams showing the first regular reflection region in case of bump deformation. FIG. 11A is similar to FIG. 7, except that the bump 2b is deformed compared to the bumps 2a and 2c. In such a case, since the apex region of the bump 2c becomes greater, the first regular reflection region corresponding thereto will also become larger. This is shown in FIG. 11B.

FIG. 11B is a diagram showing a first reflection image from the object to be inspected shown in FIG. 11A, in which the first regular reflection regions are shifted in a manner described in the first embodiment. FIG. 11B is similar to FIG. 8C except that the first regular reflection region 50b is enlarged compared to the first regular reflection regions 50a, 50c.

When the first reflection region 50b is enlarged, it is difficult to set a window. It is not so problematic when the shape of the bump 2b is deformed in a uniform manner as shown in FIG. 11B. However, if the bump has non-uniform shape, for example if the bump is deformed such that the apex part is offset from the central position of the bump, an area of the corresponding first regular reflection region 50b will increase. Also, the reflection region caused by the first reflected beam 41 from the highest part of the bump will be offset from the central position of the first regular reflection region 50b. In such a case, the setting of the window of the first embodiment is not satisfactory. That is to say, the reflection region corresponding to the highest part of the bump 2b will be located outside the window, and thus there arises a problem that the accuracy of the bump height is lowered.

In the following, the second embodiment of the present invention will be described which can solve the problem described above.

In the first embodiment, the bump shadow or the CAD data is used as mask for extracting the first regular reflection region from the first reflection image. The second embodiment differs from the first embodiment in that an image obtained from the upper part of the object to be inspected is used as a mask for extracting the first regular reflection region from the first reflection image. Therefore, since the process up to the shifting step of the first bump reflection image in the first reflection image is similar to that of the first embodiment, the description thereof is omitted.

Firstly, the second irradiation beam is irradiated vertically onto the surface of the wafer provided with bumps thereon from a position above the wafer, which is the object to be inspected. The light source may be halogen lamp or laser beam. The second irradiation beam may be irradiated from a position above the object to be inspected in a direction perpendicular to the surface of the object to be inspected and also in an oblique direction in a similar manner to the first irradiation beam. Therefore it is also possible to obtain the second reflected beam by irradiating the second irradiation beam in an oblique direction.

Next, the second reflected beam reflected at the object to be inspected is imaged at a position vertically above the object. Thus, the second reflection image is obtained.

Figure 12A:
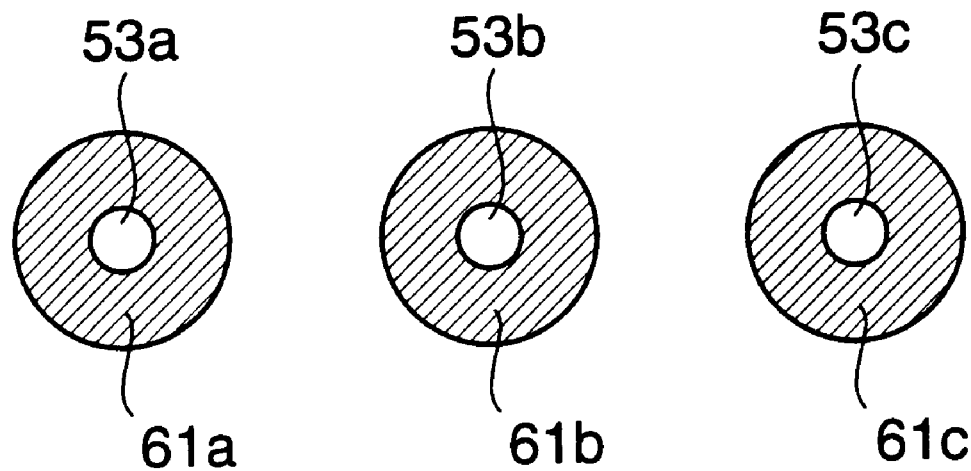
FIGS. 12A and 12B are diagrams showing a second reflection image.
Figure 12B:
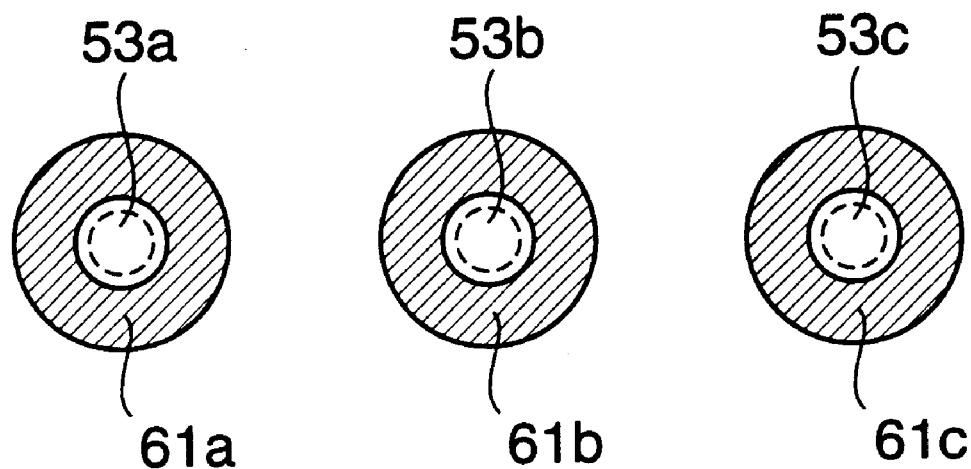

FIGS. 12A and 12B are diagrams showing the second reflection image. The second reflection image is an image produced by imaging the second reflected beam. FIGS. 12A and 12B show the second reflection images corresponding to the three bumps 2a to 2c shown in FIG. 7. FIGS. 12A and 12B show second regular reflection regions 53a to 53c which are regular reflection regions produced from the second reflected beam reflected near apices of the bumps 2a to 2c. Bump shadows 61a to 61c are regions corresponding to the positions of the bumps 2a to 2b. The bump shadows 61a to 61c are those regions in which the second irradiation beam irradiated in a vertical direction from the position above the object is not reflected back as the second irradiation beam.

In FIG. 12A, the second regular reflection regions 53a to 53c are shown with an equal size. However, if the apex part of the bump 2b is deformed as shown in FIG. 11A, since its apex part becomes larger, the second regular reflection region 53b will be enlarged correspondingly.

Also, since there is no need to use the second reflection image for detecting the heights of the bumps 2a to 2c, the incident range of the second reflected beam may be limited by reducing the NA (Numerical Aperture) of the receiving-side lens receiving the second reflected beam. Thus, an extraction of the second regular reflection region can be implemented in a more limited manner, so that an effect of the multiple reflection beam from other region can be restricted. In the present embodiment, luminance of the multiple reflected beam is provided at a value less than or equal to about 80% of the luminance of the reflected beam in the second regular reflection region.

However, if the NA of the receiving-side lens for receiving the second reflected beam is reduced, the second regular reflection region will be relatively reduced. In such a case, if the NA of the receiving-side lens for receiving the second reflected beam differs from the NA of the receiving-side lens for receiving the first reflected beam, the second regular reflection region becomes relatively small compared to the first regular reflection region.

Thus, there is a need for a compensation in which the second regular reflection region of the second reflection image shown in FIG. 12A is enlarged. This is shown in FIG. 12B. In the figure, dotted circles indicate regions corresponding to the second regular reflection regions shown in FIG. 12A. A rate of magnification can be determined by actually comparing the first regular reflection region and the second regular reflection region using a sample of a dummy. Alternatively, the rate of magnification can be derived from a ratio of the NAs of receiving-side lens used for the first reflected beam and the receiving-side lens used for the second reflected beam.

Thus, a mask can be obtained which has a window corresponding to the second regular reflection region.

In the following, a step of extracting the second regular reflection region from the first reflection image is described with reference to FIGS. 13A and 13B.

Figure 13A:
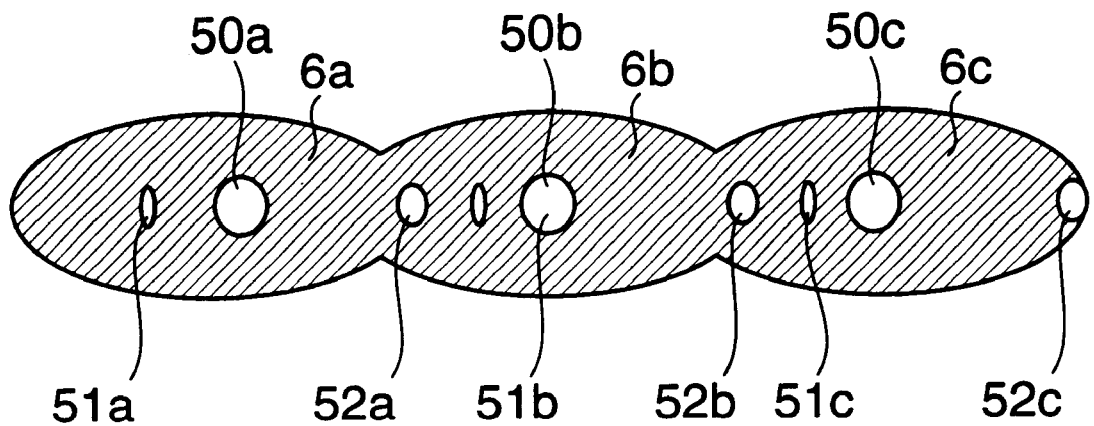
FIGS. 13A and 13B are diagrams showing how the first reflection image is masked by means of the second reflection image.

FIG. 13A is a diagram showing the first reflection image after the shifting operation of the first regular reflection regions. FIG. 13A is similar to FIG. 8C except that there are three first regular reflection regions and that other multiple reflection regions are also illustrated in the Figure.

The first reflection image is masked by the mask having the window corresponding to the second regular reflection region shown in FIG. 12B. Thus, the first regular reflection region in the first reflection image is extracted. The positioning of the first reflection image and the mask can be implemented by, for example, deriving an amount of offset of the same object between the first reflection image and the mask, and then compensating for the derived offset.

Figure 13B:
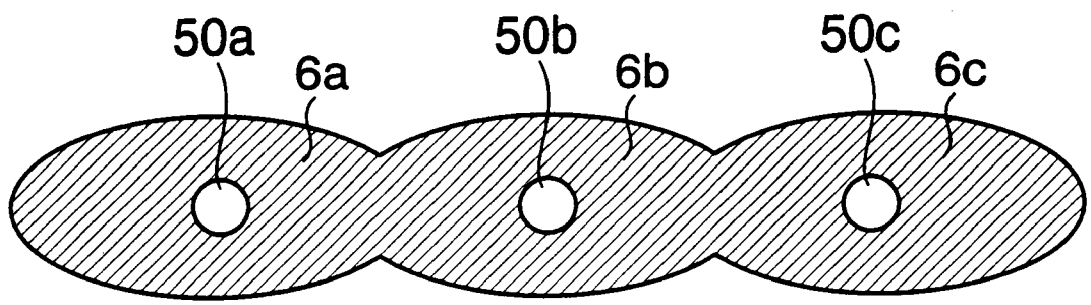

FIG. 13B is a diagram showing the extracted first reflection image.

If the bump 2b has a deformed shape as shown in FIG. 11A, the first regular reflection region 50b shown in FIG. 13A becomes larger. Also, the second regular reflection region 53b of the second reflection image serving as a mask also becomes larger. Therefore, even if a mask is used, the first regular reflection region 50b can be completely extracted while removing the multiple reflection regions. In other words, the size of the window for the first reflection image is automatically altered depending on the size of the first regular reflection region.

Therefore, even if the position of the apex of the bump 2b is offset from the central position of the bump, the first regular reflection region produced by the first reflected beam reflected at the apex can be completely extracted by the window. Accordingly, the height of the bump can be detected with high accuracy. Also, the heights of the bumps 2a to 2c can be detected from the extracted first regular reflection region in a similar manner to the steps described for the first embodiment. Therefore, the method of detecting the heights of the bumps 2a to 2c will not be described in detail.

Also, there may be a case in which the height data in the height data memory region is moved without shifting the first regular reflection region and the multiple reflection regions in the first reflection image. In such a case, in order to detect the height of the bump 2b, the height data memory region is masked by means of the mask shown in FIG. 12B, and the height data within the window 7b is extracted.

Figure 14:
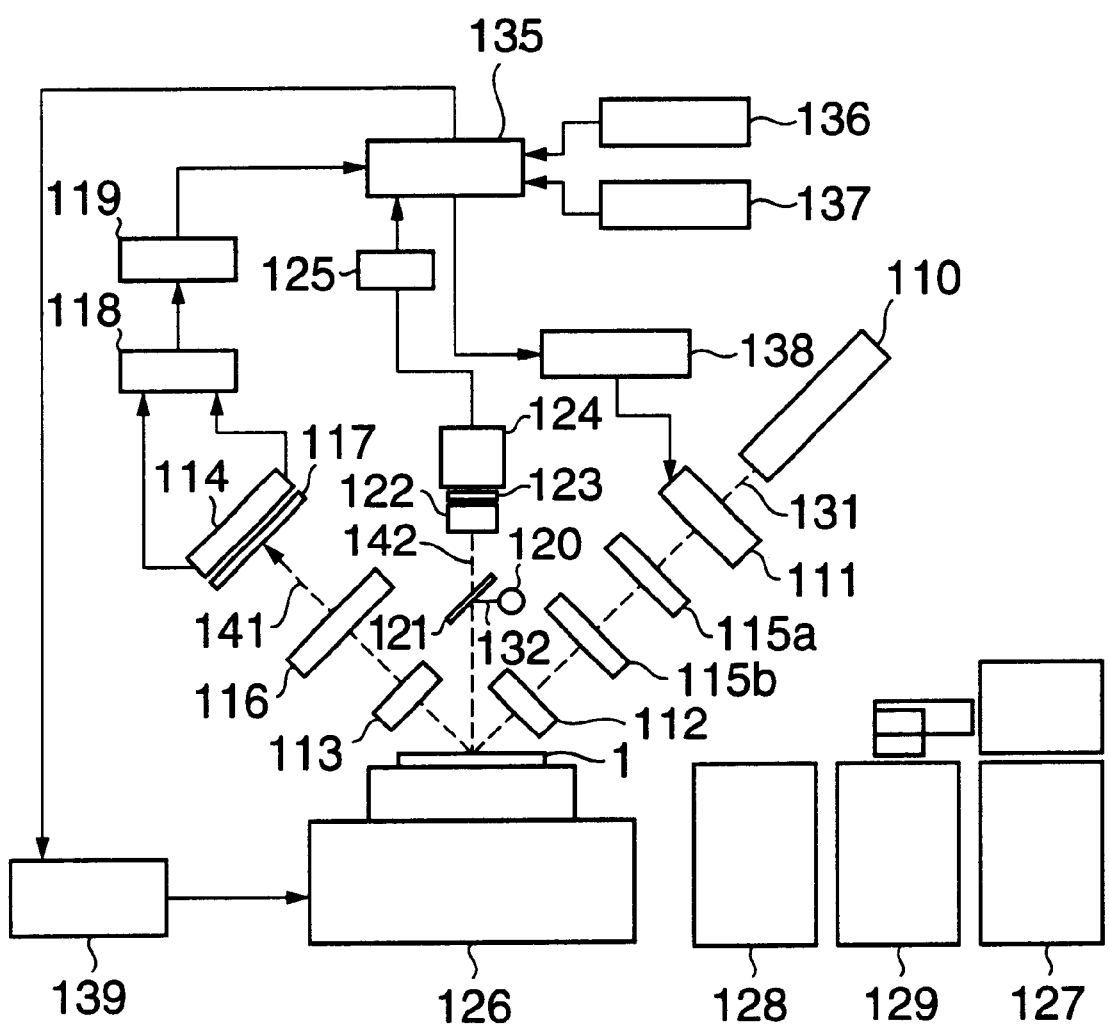
FIG. 14 is a diagram showing a bump inspection apparatus of the present invention.

Now, a third embodiment of the present invention will be described with reference to FIG. 14 showing a bump inspection apparatus.

FIG. 14 is a diagram showing the bump inspection apparatus of the present invention. FIG. 14 shows the wafer 1 provided with a plurality of bumps, not shown in the figure.

A first optical device of the apparatus of the present invention will be described in detail. A laser beam generator 110 generates a laser beam which serves as the first irradiation beam 131. A scanner 111 scans the first irradiation beam 131 in a constant direction. The scanner 111 may be an AOD (Acoustic Optical Deflector) or other type of scanner such as a polygon mirror. A first objective lens 112 is used for imaging the first irradiation beam 131 onto the surface of the wafer 1. A second objective lens 113 receives the first reflected beam 141 reflected from the surface of the wafer 1. A PSD 114 outputs an electric current corresponding to an imaging position and the brightness of the imaged light spot. Alternatively, a device such as CCD may be used as a means for detecting the position and brightness of the light spot.

Lenses 115a, 115b are used for adjusting the magnification of the scanning range of the first irradiation beam 131. A first wavelength selection filter 117 selectively transmits the first reflected beam 141. A signal processing part 118 outputs data related to the position and brightness of the light spot based on the electric current output from the PSD 114. A first memory 119 stores data output from the signal processing part 118.

Now, a second optical device of the apparatus of the present invention will be described in detail. The second optical device includes a light source 120, a half-mirror 121, an imaging lens 122, a second wavelength selection filter 123, a CCD camera 124, and a second memory 125. The light source 120 may be a halogen lamp emitting the second irradiation beam 31 to the wafer 1 via the half-mirror 121. The second imaging lens 122 receives the second reflected beam 42 from the wafer 1 and images an image of the surface of the wafer 1 onto the CCD camera 124 via the second wavelength selection filter 123. The second memory 125 stores an image output from the CCD camera 124.

Now, the apparatus of the present invention, particularly a wafer transfer robot, will be described in detail. An inspection stage 126 is constructed such that the wafer 1 can be mounted thereon and that the wafer 1 is movable in XYZr- and θ-directions. A wafer cassette 127 accommodates a plurality of wafers 1, or the objects to be inspected. An aligner 128 adjusts the rotational position of the wafer 1. A wafer transfer robot 129 removes the wafer 1 from the wafer cassette 127. After adjusting the rotational position of the wafer 1 by means of the aligner 128, the wafer transfer robot 127 transfers the wafer 1 onto the inspection stage 126. The wafer transfer robot 127 also transfers the inspected wafer 1 into the wafer cassette 127.

Now, the apparatus of the present invention, particularly a control device, will be described in detail. A control device 135 reads out the first reflection image stored in the memory 119 and the second reflection image stored in the memory 125, and implements predetermined processes. A terminal 136 includes a keyboard for giving instructions of the processes to the control device 135 or a display device for displaying the result of the processes from the control device 135. An external storage device 137 may be used for storing the CAD data such as the position of the bump provided on the wafer 1 or for storing the results of the inspection. A modulation control circuit 138 controls the AOD 111 so that the wafer 1 can be scanned with an appropriate amount of light and scanning speed. A stage controller 139 controls the speed by moving the inspection stage 126 in a sub-scanning direction, each time the AOD scans in a main-scanning direction, based on the signals supplied from the control device 135.

In the following, an operation of the above-described bump inspection apparatus will be described in detail.

First, an operation of the bump inspection apparatus for the method of inspecting the bumps in accordance with the first embodiment will be described. In such an operation, the above-described second optical device and/or the wavelength selection filter 117 can be dispensed with.

The first optical device operates as follows. The laser beam generator 110 emits a laser beam having a predetermined wavelength which serves as the first irradiation beam 31. The first irradiation beam 31 scans the surface of the wafer 1 provided with the plurality of bumps in the main-scanning direction using the AOD 111, the lenses 115a, 115b and the first objective lens 112.

The first reflected beam 41 reflected at the surface of the wafer 1 is incident on the second objective lens 112 and the imaging lens 116, passes through the wavelength selection filter 117 and then imaged on the PSD 114. The signals output from the PSD 114 are converted in the signal processing part 118 into data signals representing the brightness and height. The first memory 119 sequentially stores the brightness and height data for each scanning position, and forms the first reflection image and the height data memory region.

Next, an operation of the control device 135 will be described.

First, the control device 135 controls the scanning timings of the AOD 111 via the modulation control circuit 138. Simultaneously, the control device 35 moves the inspection stage 126 in the sub-scanning direction via the stage controller 139, each time the AOD 111 scans in the main-scanning direction. Thus, the wafer 1 is scanned by the first irradiation beam 31 for the entire area to be inspected. The control device 135 reads out the first reflection image and the height data stored in the memory 119 and also the CAD data related to the position of the bump stored in the external storage device 137. The control device 135 then refers to the position of the bump obtained from the data and moves the first regular reflection region in the first reflection image according to the method of the first embodiment. Thus, the first regular reflection region is extracted by masking the first reflection image and then the bump height is detected.

The terminal 136 gives instructions to the control device 135 where appropriate. The control device 135 announces data such as the inspection result to the terminal 136 and to the external storage device 137. The inspection result is displayed and printed at the terminal 136 and is stored in the external storage device 137.

Now, an operation of related to the wafer transfer robot will be described.

The wafer transfer robot 129 transfers the plurality of wafers 1 stored in the wafer cassette to the aligner 128. The aligner 128 adjusts the rotational position of the wafer 1. The wafer transfer robot 129, after position adjustment, transfers the wafer 1 to the inspection stage 126. Also, The wafer transfer robot 129, after the inspection, transfers the wafers 1 from the inspection stage 126 to the wafer cassette 127 in which the wafers 1 are accommodated. These steps are repeated.

Now, an operation of the bump inspection apparatus for the method of inspecting the bumps in accordance with the second embodiment will be described in detail. This operation is similar to the operation in accordance with the first embodiment except that the second optical device is used in the present embodiment. Therefore, only those operations related to the second optical device will be described in detail.

First, an operation of the second optical device will be described. Also, it is to be noted that the operation of the second optical device and the first optical device are implemented simultaneously.

The light source 120 emits the second irradiation beam 32 having a wavelength different from the wavelength of the first irradiation beam 31. Thus, the first reflected beam 41 and the second reflected beam 42 may be selectively transmitted by means of the wavelength selection filters 117, 123. The emitted second irradiation beam 32 is irradiated onto the surface of the wafer 1 via the half-mirror 121. The second reflected beam 42, which have been reflected on the surface of the wafer 1, is incident on the imaging lens 122 via the half-mirror 121. Only the second reflected beam 42 is selectively transmitted at the wavelength selection filter 123. Then, the second reflected beam 42 is imaged on the CCD camera. The CCD camera sends the signals of the imaged image to the second memory 125. This image will be stored in the second memory 125 as an original image of the second reflection image.

Next, an operation of the control device 135 will be described. It is to be noted that the scanning operation is controlled in a manner described above.

The control device 135 moves the first regular reflection region in the first reflection image according to the operation described in relation to the second embodiment. The control device 135 masks the first reflection image by means of the second reflection image in a manner shown in the second embodiment. Thus, the first regular reflection region is extracted and the height of the bump is detected.

Also, the control device 135 moves the inspection stage 126 via the stage controller 139 so as to control an attitude of the wafer 1 based on the second reflection image. Thus, the diameter of the bump formed on the wafer 1 is measured and the detection of extra bumps and bump deficiency is implemented.

Further, the present invention is not limited to these embodiments, but variations and modifications may be made without departing from the scope of the present invention.

The present application is based on Japanese priority application No. 11-099440 filed on Apr. 6, 1999, the entire contents of which are hereby incorporated by reference.

What is claimed is:

1. A method of inspecting bumps provided on a surface of an object to be inspected, said method comprising the steps of:

a) irradiating a first irradiation beam on said object in an oblique direction at a predetermined angle with respect to said surface;

b) imaging a first reflected beam from said object to obtain a first reflection image including a first regular reflection region, said first regular reflection region being produced by a part of the first reflected beam reflected near an apex of the bump;

c) obtaining height data of said bump that corresponds to said first regular reflection region;

d) calculating a shifted position of said first regular reflection region on the basis of said height data and said predetermined angle; and e) determining whether said calculated shifted position of said first regular reflection region is within a region in said first reflection image to detect a height of the bump, said determining step comprising:
positioning the first reflection image with predetermined data; and
setting a central position of the region according to the position information of the bump in the predetermined data.

2. The method as claimed in claim 1,
wherein said step c) is repeated for each of predetermined pixel blocks, and
in said step c), a position of the pixel block is shifted in said first reflection image in a direction opposite to the direction of irradiation of said first irradiation beam by a value given by:

$$h/\tan(\theta);$$

h being a value of said height data corresponding to a pixel block within said first reflection region,
θ being said predetermined angle.

3. The method as claimed in claim 2, further comprising the steps of:

f) irradiating a second irradiation beam from a position above said surface of said object;

g) imaging a second reflected beam from said object and obtaining a second reflection image; and h) determining said predetermined position based on a second regular reflection region in said second reflection image, said second regular reflection region being produced by a part of the second reflected beam reflected at the bump.

4. The method as claimed in claim 3, wherein a wavelength of said first irradiation beam is different from a wavelength of said second irradiation beam, and
said first reflected beam and said second reflected beam being selectively obtained via wavelength selection filters, respectively, from the reflected beam from said object.

5. An apparatus for inspecting a bump provided on a surface of an object to be inspected, comprising:
a first optical device including a first beam emitting part irradiating a first irradiation beam on said object in an oblique direction, an imaging part via which said first irradiation beam is imaged on said object, a first selective filter transmitting a first reflected beam from said object, a position sensitive detector outputting an electric current corresponding to the brightness and position of said first reflected beam, and a first signal processing part outputting data representing first regular reflection region data in a first reflection image and data representing the height of the bump based on said electric current; and a control device connected to a main-scanning operation controlling part, a sub-scanning operation controlling part and a first memory in which the first reflection image and the bump height data are stored, said control device calculating a shifted position of said first regular reflection region on the basis of said height data and said predetermined angle and determining whether said calculated shifted position of said first regular reflection region is within a region in said first reflection image to detect a height of the bump, said determining comprising:

positioning the first reflection image with predetermined data; and setting a central position of the region according to the position information of the bump in the predetermined data.

6. The apparatus as claimed in claim 5, further comprising:

a second optical device including a second light emitting part irradiating a second irradiation beam on said object from a direction vertically above said object, a second selective filter transmitting a second reflected beam from said object, an imaging part via which a second reflected beam of said second irradiation beam reflected at the object is imaged on an image acquisition part so as to form second reflection image, wherein said control device defines said predetermined region based on a second regular reflection region within said second reflection image, said second regular reflection region being produced by a part of the reflected beam reflected from the bump.

7. A method of inspecting bumps provided on a surface of an object to be inspected, said method comprising the steps of:

a) irradiating a first irradiation beam on said object in an oblique direction at a predetermined angle with respect to said surface;

b) imaging a first reflected beam from said object to obtain a first reflection image including a reflection region, said reflection region being produced by a part of the first reflected beam from the bump;

c) obtaining height data of said bump that corresponds to said first regular reflection region;

d) calculating a shifted position of said first regular reflection region on the basis of said height data and said predetermined angle;

e) masking said first reflection image after said step d); and f) determining whether said calculated shifted position of said first regular reflection region is within a predetermined region in said first reflection image.

8. A method of inspecting bumps provided on a surface of an object to be inspected, said method comprising the steps of:

a) irradiating a first irradiation beam on said object in an oblique direction at a predetermined angle with respect to said surface;

b) imaging a first reflected beam from said object to obtain a first reflection image including a first regular reflection region, said first regular reflection region being produced by a part of the first reflected beam reflected near an apex of the bump;

c) obtaining height of said bump that corresponds to said first regular reflection region;

d) calculating a shifted position of said height data corresponding to said first regular reflection region on the basis of said height data and said predetermined angle; and e) determining whether said calculated shifted position of said first regular reflection region is within a predetermined region in said first reflection image.

9. An apparatus for inspecting bumps provided on a surface of an object to be inspected, said apparatus comprising:

a first part for irradiating a first irradiation beam on said object in an oblique direction at a predetermined angle with respect to said surface;

a second part for imaging a first reflected beam from said object to obtain a first reflection image including a first regular reflection region, said first regular reflection region being produced by a part of the first reflected beam reflected near an apex of the bump;

a third part for obtaining height data of said bump that corresponds to said first regular reflection region;

a fourth part for calculating a shifted position of said first regular reflection region on the basis of said height data and said predetermined angle; and a fifth part for determining whether said calculated shifted position of said first regular reflection region is within a region in said first reflection image to detect a height of the bump, said determining comprising:

positioning the first reflection image with a predetermined data; and setting a central position of the region according to the position information of the bump in the predetermined data.

10. A method of inspecting bumps provided on a surface of an object to be inspected, said method comprising the steps of:

a) irradiating a first irradiation beam on said object in an oblique direction at a predetermined angle with respect to said surface;

b) imaging a first reflected beam from said object to obtain a first reflection image including a first regular reflection region, said first regular region being produced by a part of the first reflected beam reflected near an apex of the bump;

c) obtaining height data of said bump that corresponds to said first regular reflection region;

d) calculating a shifted position of said first regular reflection region on the basis of said height data and said predetermined angle; and e) determining whether said calculated shifted position of said first regular reflection region is within a predetermined region in said first reflection image to detect a height of the bump, wherein said predetermined region has a shape corresponding to a shape of the bump.

11. The method as claimed in claim 10, wherein said predetermined region corresponds to a central region of said bump determined from said first reflection image or CAD data prepared in advance.

12. A method of inspecting bumps provided on a surface of an object to be inspected, said method comprising the steps of:

a) irradiating a first irradiation beam on said object in an oblique direction at a predetermined angle with respect to said surface;
b) imaging a first reflected beam from said object to obtain a first reflection image including a first regular reflection region, said first regular reflection region being produced by a part of the first reflected beam reflected near an apex of the bump;
c) obtaining height data of said bump that corresponds to said first regular reflection region;
d) calculating a shifted position of said first regular reflection region on the basis of said height data and said predetermined angle;
e) determining whether said calculated shifted position of said first regular reflection region is within a predetermined region in said first reflection image;
f) irradiating a second irradiation beam from a position above said surface of said object;
g) imaging a second reflected beam from said object and obtaining a second reflection image; and
h) determining said predetermined position based on a second regular reflection region in said second reflection image, said second regular reflection region being produced by a part of the second reflected beam reflected at the bump.

* * * * *